US010881552B2

(12) United States Patent
Rathjen

(10) Patent No.: US 10,881,552 B2
(45) Date of Patent: Jan. 5, 2021

(54) VACUUM DEVICE AND METHOD OF MONITORING AN OPHTHALMOLOGICAL PATIENT INTERFACE

(71) Applicant: Ziemer Ophthalmic Systems AG, Port (CH)

(72) Inventor: Christian Rathjen, Bremen (DE)

(73) Assignee: Ziemer Ophthalmic Systems AG, Port (CH)

( * ) Notice: Subject to any disclaimer, the term of this patent is extended or adjusted under 35 U.S.C. 154(b) by 231 days.

(21) Appl. No.: 15/638,951

(22) Filed: Jun. 30, 2017

(65) Prior Publication Data
US 2018/0000641 A1    Jan. 4, 2018

(30) Foreign Application Priority Data

Jul. 4, 2016 (EP) .................................... 16177791

(51) Int. Cl.
*A61F 9/008* (2006.01)
*A61F 9/009* (2006.01)
*A61B 3/113* (2006.01)

(52) U.S. Cl.
CPC .............. *A61F 9/009* (2013.01); *A61B 3/113* (2013.01); *A61F 9/008* (2013.01); *A61F 9/00825* (2013.01); *A61F 2009/00846* (2013.01)

(58) Field of Classification Search
CPC combination set(s) only.
See application file for complete search history.

(56) References Cited

U.S. PATENT DOCUMENTS

| | | | | |
|---|---|---|---|---|
| 7,166,117 B2* | 1/2007 | Hellenkamp | ........... | A61F 9/013 606/166 |
| 8,733,934 B2* | 5/2014 | Vogler | .................... | A61B 3/102 351/200 |
| 9,987,165 B2* | 6/2018 | Gooding | ............. | A61M 1/0052 |
| 10,195,085 B2* | 2/2019 | Campos | .................. | A61F 9/009 |
| 2014/0128821 A1* | 5/2014 | Gooding | ............. | A61M 1/0052 604/290 |

(Continued)

FOREIGN PATENT DOCUMENTS

EP        2913036 A1     9/2015
WO    2016/100439 A1     6/2016

OTHER PUBLICATIONS

Jan. 31, 2017—(EP) Search Report—App 16177791.7.

*Primary Examiner* — Michael W Kahelin
*Assistant Examiner* — Shirley X Jian
(74) *Attorney, Agent, or Firm* — Banner & Witcoff, Ltd.

(57) ABSTRACT

A vacuum device comprises a vacuum generator and a vacuum interface for fluidically coupling the vacuum generator to a vacuum cavity for affixing an ophthalmological patient interface on a patient's eye. The vacuum device comprises a movement detector which is configured to detect movements of the patient's eye and a control unit that is configured to detect a faulty fluidic coupling of the vacuum cavity on the basis of a pressure that is ascertained by a coupled pressure sensor and to produce a control signal for interrupting an ophthalmological treatment that is carried out by an ophthalmological treatment device if an eye movement is detected by the movement detector at the same time as the detected faulty fluidic coupling of the vacuum cavity.

23 Claims, 4 Drawing Sheets

(56) References Cited

U.S. PATENT DOCUMENTS

| | | | |
|---|---|---|---|
| 2014/0128852 A1* | 5/2014 | Gooding | A61F 9/009 606/4 |
| 2015/0190278 A1* | 7/2015 | Gooding | A61F 9/009 606/4 |
| 2016/0106582 A1 | 4/2016 | Campos et al. | |
| 2016/0175146 A1* | 6/2016 | Gooding | A61F 9/008 606/4 |
| 2017/0311796 A1* | 11/2017 | Walsh | A61B 3/102 |

* cited by examiner

VACUUM DEVICE AND METHOD OF MONITORING AN OPHTHALMOLOGICAL PATIENT INTERFACE

This application claims priority to European Patent Application No. 16177791.7 filed Jul. 4, 2016. The disclosure of this application is expressly incorporated herein by reference in its entirety.

TECHNICAL FIELD

The present invention relates to a vacuum device and a method of monitoring an ophthalmological patient interface. The present invention relates, in particular, to a vacuum device for affixing an ophthalmological patient interface on a patient's eye and a method of monitoring the ophthalmological patient interface.

PRIOR ART

The use of radiation generators, in particular lasers, for treating and/or diagnosing eye tissue is known. Corresponding devices, such as ophthalmological laser apparatuses, have e.g. a base machine with a laser light source for producing laser pulses, e.g. femtosecond laser pulses, and an application head with a projection lens which, for the treatment, is coupled to the patient's eye. The application head may be movably connected to the base machine, e.g. via an articulated arm, wherein the articulated arm may simultaneously serve for the optical beam guidance from the laser light source to the application head. A corresponding arrangement is disclosed in e.g. EP 1731120. Moreover, there are machines in which the application head is integrated in the base machine or in which other device arrangements are provided.

The application head is mechanically and optically coupled to the patient's eye, e.g. to the cornea and/or the sclera of the patient's eye, via a patient interface, wherein the patient interface may comprise a transparent contact body, by means of which the laser pulses emerging from the projection lens are guided in a focused manner onto or into the eye and which, by means of a mechanical contact with the cornea, affixes the latter in relation to the patient interface and the projection lens. As an alternative to coupling by means of a contact body, provision can be made for liquid coupling, wherein a coupling liquid, e.g. physiological saline solution, is situated between cornea and projection lens. Corresponding patent interfaces are known e.g. from EP 2030598.

The coupling of the patient interface to the patient's eye can be effectuated by means of a vacuum and a vacuum cavity of the patient interface. The vacuum cavity is typically a suction ring that is placed onto the cornea. Most suction rings have two sealing lips. The lips may be applied to the sclera, the sclera and the cornea or only to the cornea. Furthermore, there are variants which only have one ring and produce a vacuum over the whole eye, or variants consisting of a plurality of suction chambers/suction cups. The suction ring is the most common method of attachment; however, there are also other known solutions. In any case, the coupling to the patient's eye is brought about by a vacuum in at least one vacuum cavity of the patient interface, wherein the vacuum cavity lies, with sealing being effectuated along the circumference thereof, on the patient's eye and the patient interface thus couples on the patient's eye in a fluidically sealing manner and seals the latter from the surroundings. The vacuum can be produced by a vacuum generator, in particular a vacuum pump. In known systems, the patient interface is coupled to the application head by means of e.g. screw-in connections, bayonet connections or vacuum couplings.

US 2002/0120285 A1 discloses a blade guidance for an ophthalmological surgical instrument which is affixed to the patient's eye by means of a vacuum and which measures the contact pressure between the sclera and the blade guidance.

US 2002/0198553 A1 describes a patient interface and a vacuum device with a fluidic pressure measurement, with the connection to the patient interface being brought about by means of a common fluidic line.

WO 2008/150330 discloses a patient interface which is provided for coupling to the patient's eye by means of a vacuum and which has a two-part embodiment, wherein contact pressure sensors are arranged at a coupling point between the parts, said contact pressure sensors capturing a contact pressure between the parts.

2016/0106582 describes a system for detecting a loss of vacuum during a laser eye treatment, in which the laser radiation is guided through a liquid medium of a liquid-filled patient interface. A plurality of inputs are monitored in the system as per 2016/0106582 in order to detect a leak. The inputs comprise a video stream of the eye in order to search for air bubbles in the liquid medium; force sensors on the patient interface which detect movements of the patient in order to use these as early indications for patient unrest and as a prediction for a possibly upcoming vacuum leak; and vacuum sensors which directly measure the extent of the suction force between the patient interface and the eye. The system according to 2016/106582 comprises control electronics which stop or delay the laser treatment if an aggregate of all three inputs corresponds to a threshold that indicates a significant vacuum leak. Depending on how the aggregate is defined, it is possible, on the one hand, for a loss of vacuum without a bubble formation connected therewith not to be correctly detected in the case of a comparatively less sensitive setting or, on the other hand, for a brief, temporary loss of pressure to unnecessarily lead to an interruption or termination of the laser treatment in the case of a comparatively more sensitive setting.

EP 2913036 describes an ophthalmological laser system with a vacuum-based patient interface (eyeball fixation unit), in which the vacuum is monitored by means of pressure sensors when the patient interface is applied onto the eyeball in order to identify the contact with the eyeball or an excessively high pressure on the eyeball. EP 2913036 moreover describes the detection of the movement of eye features. If the eyeball moves on account of an interruption in the suction, a control unit is configured to stop laser irradiation on the basis of detection results. In accordance with EP 2913036, the suction state is detected promptly in such a case when compared with the monitoring of the suction ring by means of pressure sensors.

SUMMARY OF THE INVENTION

It is an object of the present invention to propose a vacuum device for affixing an ophthalmological patient interface on a patient's eye and a method of monitoring the ophthalmological patient interface, said vacuum device and said method not having at least some of the disadvantages of known systems. In particular, it is an object of the present invention to propose a vacuum device and a method of monitoring the ophthalmological patient interface which avoids unnecessary interruptions of laser treatments wherever possible.

In accordance with the present invention, these objects are achieved by the features of the independent claims. Further advantageous embodiments moreover emerge from the dependent claims and the description.

A vacuum device for affixing an ophthalmological patient interface on a patient's eye comprises a vacuum generator and a vacuum interface for fluidic coupling of the vacuum generator on a vacuum cavity of the patient interface.

In particular, the aforementioned objects are achieved by the present invention by virtue of the vacuum device comprising an internal pressure sensor that is fluidically coupleable to the patient interface and/or a pressure-measuring interface for a signal-coupling of an external pressure sensor of the patient interface and moreover having a movement detector which is configured to detect movements of the patient's eye. Moreover, the vacuum device comprises a control unit which is configured to detect a faulty fluidic coupling of the vacuum cavity on the basis of the pressure that is ascertained by the coupled pressure sensor and to produce a control signal for interrupting an ophthalmological treatment that is carried out by an ophthalmological treatment device if an eye movement is detected by the movement detector at the same time as the detected faulty fluidic coupling of the vacuum cavity.

In an embodiment variant, the control unit is configured to produce a warning signal without interrupting the ophthalmological treatment if no eye movement is detected during a detected faulty fluidic coupling of the vacuum cavity.

In an embodiment variant, the movement detector comprises a video sensor and a processing unit that is connected to the video sensor and configured to detect the eye movements on the basis of video signals supplied by the video sensor.

In an embodiment variant, the movement detector is configured to detect movements of the patient's eye which move the patient's eye relative to a static observation axis.

In particular, the movement detector is configured to detect relative movements of the patient's eye during the ophthalmological treatment that is carried out by the ophthalmological treatment device. By way of the detection of eye movements relative to the projection lens or the optical axis of the projection lens of the ophthalmological treatment device that is carried out during the ophthalmological treatment, the movement detector (in the docked state) facilitates the detection of movements of the patient's eye relative to the patient interface.

In an embodiment variant, the control unit is configured to produce the control signal for interrupting the ophthalmological treatment if the movement detector detects an eye movement that lies over a defined tolerance threshold.

In an embodiment variant, the vacuum device comprises a pressure sensor interface that has a fluidic connection to the internal pressure sensor, said pressure sensor interface being configured to fluidically couple the internal pressure sensor to the patient interface, separately from the vacuum interface.

In an embodiment variant, the pressure-measuring interface is configured for signal-coupling of an external contact pressure sensor that is arranged at the patient interface.

In an embodiment variant, the control unit is configured to detect the faulty fluidic coupling of the vacuum cavity by detecting a deviation between the pressure that is ascertained by means of the coupled pressure sensor and a reference pressure, and/or by detecting a drop in the pressure as a function of time.

In an embodiment variant, the vacuum device comprises a second pressure sensor that is fluidically coupled to the vacuum interface and connected to the control unit and the control unit is configured to detect the faulty fluidic coupling of the vacuum cavity by comparing the ascertained pressure with a second pressure that is ascertained by the second pressure sensor.

In an embodiment variant, the movement detector comprises a sensor device that is configured to detect the eye movements on the basis of changes in the distance of the patient's eye relative to the patient interface.

In an embodiment variant, the control unit is configured to produce a correction signal for repositioning and continuing the ophthalmological treatment on the basis of a detected eye movement if a termination of the eye movement and no faulty fluidic coupling of the vacuum cavity are detected.

In addition to the vacuum device for affixing an ophthalmological patient interface on a patient's eye, the present application also relates to a method of monitoring the ophthalmological patient interface which is affixed on the patient's eye by means of a vacuum that is produced by the vacuum generator in a vacuum cavity of the patient interface. The method comprises the following steps: ascertaining a pressure in the vacuum cavity by means of a pressure sensor that is fluidically coupled to the patient interface and/or by means of a contact pressure sensor of the patient interface; detecting movements of the patient's eye by means of a movement detector; detecting a faulty fluidic coupling of the vacuum cavity at the vacuum generator by way of a control unit on the basis of the ascertained pressure; and producing a control signal by way of the control unit for interrupting an ophthalmological treatment that is carried out by an ophthalmological treatment device if an eye movement is detected by the movement detector at the same time as the detected faulty fluidic coupling of the vacuum cavity.

In an embodiment variant, the control unit produces a warning signal without interrupting the ophthalmological treatment if no eye movement is detected during a detected faulty fluidic coupling of the vacuum cavity.

In an embodiment variant, there is a video capture of the patient's eye by a video sensor and the eye movements are detected by the control unit on the basis of the video capture.

In one embodiment variant, the control signal produces the control signal for interrupting the ophthalmological treatment if the movement detector detects an eye movement that lies over a defined tolerance threshold.

The present application also relates to an ophthalmological treatment device comprising a laser system for the ophthalmological treatment of a patient's eye, an application head and a patient interface for attaching the application head to the patient's eye. Moreover, the ophthalmological treatment device comprises the aforementioned vacuum device for affixing the ophthalmological patient interface on the patient's eye.

BRIEF DESCRIPTION OF THE DRAWINGS

Below, an embodiment of the present invention is described on the basis of an example. The example of the embodiment is illustrated by the following attached figures.

WAYS OF IMPLEMENTING THE INVENTION

Figure 1:
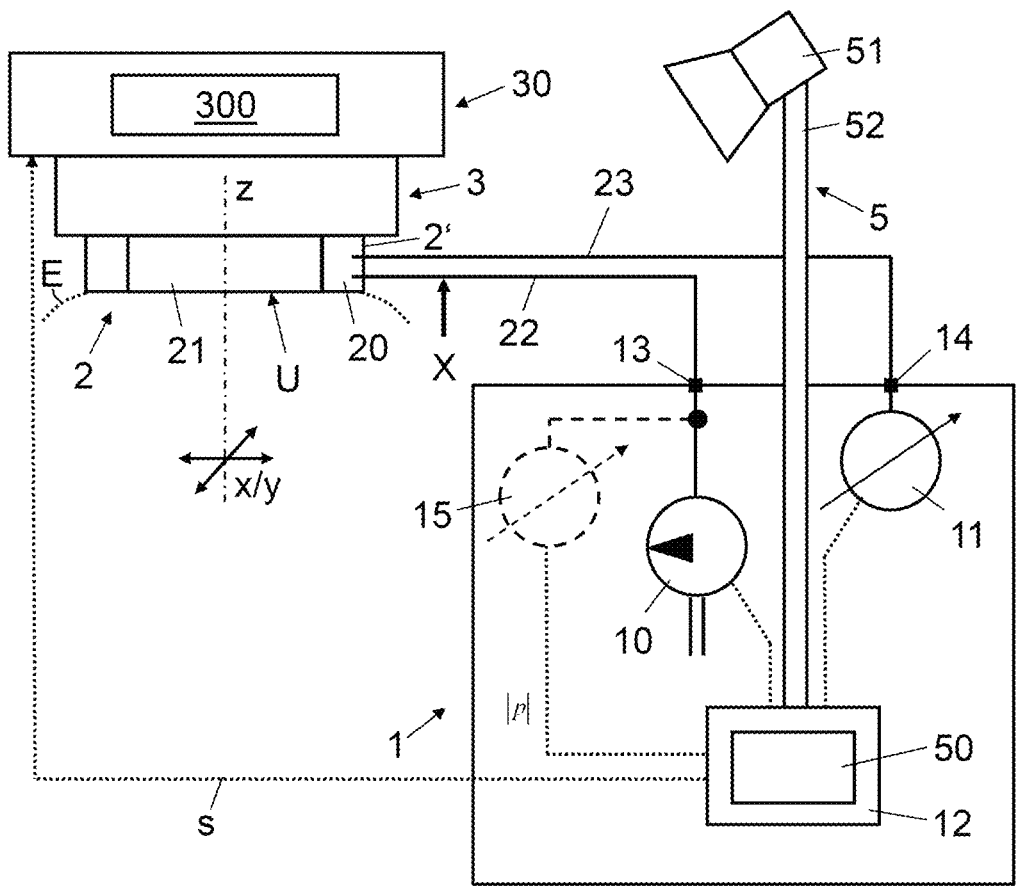
FIG. 1: shows a block diagram of an ophthalmological arrangement comprising a vacuum device and a patient interface that is fluidically coupled therewith.

In FIG. 1, the reference sign 1 denotes a vacuum device and the reference sign 2 denotes a patient interface connected to the vacuum device 1, in a schematic cross section. For the purposes of carrying out an ophthalmological treatment, the patient interface 2 is coupled to an ophthalmological application head 3 of an ophthalmological treatment device 30. Together, the vacuum device 1 and the patient interface 2 form an ophthalmological arrangement. The ophthalmological treatment device 30 comprises a laser system 300 which is configured to produce laser pulses for the purposes of an ophthalmological treatment of the patient's eye E and to radiate said laser pulses in focus onto and into the patient's eye E via the application head 3 and the patient interface 2.

In the application state, the patient interface 2 rests with its lower side U of the patient interface body 2' on the cornea of the patient's eye E. The patient interface body 2' of the patient interface 2 has an e.g. cylindrical interior 21 which, in the application state, is situated between the corneal surface of the patient's eye E and the application head 3 and which may be filled with e.g. physiological saline solution as a coupling liquid and as an optical transfer medium. Arranged concentrically around the interior 21 there is a suction ring which likewise rests on the cornea of the patient's eye E in the application state and the interior of said suction ring forms at least one vacuum cavity 20 which e.g. has a ring-shaped configuration. For the purposes of coupling the patient interface 2 or the patient interface body 2' to the patient's eye E, a vacuum is produced in the vacuum cavity 20, said vacuum thus affixing the patient interface 2 on the patient's eye E.

The vacuum device 1 comprises a vacuum generator 10 which is typically formed by a vacuum pump, and a vacuum interface 13 that is fluidically coupled to the vacuum generator 10. The vacuum generator 10 and the vacuum cavity 20 of the patient interface 2 are fluidically coupled to one another by way of the vacuum connecting line 22. On the side of the patient interface 2, the vacuum connecting line 22, with one end, is fluidically coupled to the vacuum cavity 20 of the patient interface 2 in a removable or secured manner. On the side of the vacuum device 1, the vacuum connecting line 22, with the other end thereof, is fluidically coupled to the vacuum generator 10 via the vacuum interface 13.

The vacuum device 1 moreover comprises a fluidic pressure sensor 11 and a pressure sensor interface 14 which is fluidically coupled to the pressure sensor 11. The pressure sensor 11 and the vacuum cavity 20 of the patient interface 2 are fluidically coupled to one another by way of the pressure sensor connecting line 23, separately from the vacuum connecting line 22. On the side of the patient interface 2, the pressure sensor connecting line 23, with one end, is fluidically coupled to the vacuum cavity 20 of the patient interface 2 in a removable or secured manner. On the side of the vacuum device 1, the pressure sensor connecting line 23, with the other end thereof, is fluidically connected to the pressure sensor 11 via the pressure sensor interface 14.

The vacuum connecting line 22 and the pressure sensor connecting line 23 are fluidically coupled to the vacuum cavity 20 with one end, separately in each case, with the fluidically separate coupling in each case extending along the entire fluidic path and, in particular, up to the vacuum cavity 20.

By way of example, the vacuum interface 13 and the pressure sensor interface 14 are embodied as detachable fluidic plug-in connectors or coupling units, e.g. fluidic coupling connectors. The vacuum connecting line 22 and the pressure sensor connecting line 23 each have corresponding fluidic coupling elements, e.g. fluidic plug-in connectors, which are provided for detachable coupling to the device-side vacuum interface 13 or the device-side pressure sensor interface 14.

Moreover, the vacuum device 1 comprises a control unit 12 which comprises a processing unit 50 for controlling the function of the vacuum device 1. The processing unit 50 is embodied as an electronic circuit and comprises a logic circuit, e.g. an ASIC (application specific integrated circuit) or an FPGA (field programmable gate array), and/or one or more microprocessors with stored program code for controlling the microprocessors in such a way that these carry out the functions, described below, of the control unit 12 and of the movement detector 5 that is presented below.

As schematically illustrated in FIGS. 1 to 4, the vacuum device 1 is provided with a movement detector 5, the latter being configured to detect movements of the patient's eye E. The movement detector 5 is configured to detect movements of the patient's eye E relative to a static observation axis, e.g. the optical axis z of a projection lens of the ophthalmological treatment device 30, both in movement directions (x, y) which extend in a xy-plane that is normal to the observation or optical axis z and which correspond to a displacement of the patient's eye E (or a corresponding slip of the patient interface 2) in relation to the observation or optical axis z and in movement directions (z) which extend along the observation or optical axis z and which correspond to a change in distance from the patient interface 2 or from the application head 3 (or correspond to lifting of the patient interface 2). Depending on the embodiment variant, the movement detector 5 comprises one or more sensor devices 51 for imaging or beam-based detection methods, e.g. a video sensor for the video capture of the patient's eye E and/or light transmitters and light detectors for beam-based OCT (optical coherence tomography) systems or triangulation systems, etc. By way of example, the video sensor is embodied as a CCD (charge-coupled device) camera and supplies video signals of the monitored patient's eye E. Depending on the embodiment variant and/or the configuration, the sensor device 51 is attached to the vacuum device 1, for example by means of a carrier, or it is securely or removably attached to, or integrated into, the ophthalmological treatment device 30, for example to, or into, the application head 3. The measurement signals, e.g. video signals, are continuously transmitted by the sensor device 51 by way of a measurement signal line 52, e.g. a video signal line, to the processing unit 50, where they are evaluated for the purposes of detecting eye movements. For the purposes of detecting eye movements on the basis of video signals, the processing unit 50, in the video frames of the patient's eye E defined by the video signals, continuously ascertains local changes of reference features of the relevant patient's eye E, e.g. pupil, iris and/or characteristic features of details of the iris, in respect of previously captured and stored reference positions. For the purposes of detecting eye movements by means of OCT, repeated spatial scans of the patient's eye E are carried out, e.g. circular sections through the cornea or any other defined volume scan of a defined region of the eye, and said scans are continuously examined by the processing unit 50 in respect of deviations in terms of content (at the same positions), said deviations indicating an eye movement. As a result, the processing unit 50 recognizes and detects movements of the patient's eye E relative to the static observation or optical axis z. As a result of the beam-based OCT or triangulation methods, eye movements in the z-direction are also detected by changes in the distance between the patient's eye E and the patient interface 2 or the application head 3, in addition to lateral displacements in the x/y-direction. A person skilled in the art will understand that use can be made of further movement detectors 5 for detecting movements of the patient's eye E relative to the patient interface in the lateral x/y-direction or with changes of distance in the z-direction. In one embodiment variant, the movement detector 5 or the processing unit 50 displays a detected eye movement if changes in the position of eye structures which lie above a defined tolerance threshold are detected, for example above a defined distance limit d, e.g. d>1 mm, in respect of the observation axis z in the x-, y- or z-direction.

Figure 2:
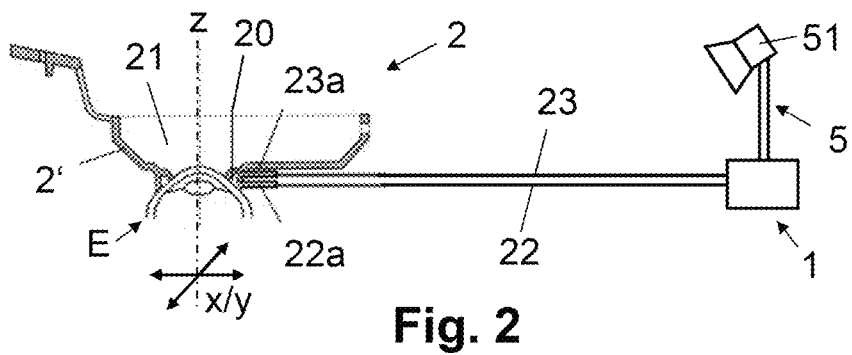
FIG. 2: schematically shows, in a cross section, an embodiment of a patient interface that is affixed to a patient's eye, said patient interface being fluidically coupled to a vacuum device.

FIG. 2 schematically illustrates part of a patient interface 2 together with a patient's eye E. The patient interface 2 has a patient interface body 2' with a ring-shaped vacuum cavity 20 and an interior 21. Separately, two fluidic connection nozzles 22a, 23a open into the vacuum cavity 20, said connection nozzles, in a manner known per se, being connected in a fluidically tight manner to the patient-interface-side ends of the vacuum connecting line 22 and of the pressure sensor connecting line 23, for example by way of adhesive bonding, ultrasonic welding or a frictional fit. The other ends of the fluidic vacuum connecting line 22 and pressure sensor connecting line 23 are coupled to the vacuum device 1, for example by means of plug-in connectors which, during operation, are coupled to an appropriate patient interface coupling unit of the vacuum device 1 in the form of a fluidic coupling connector.

Figure 3:
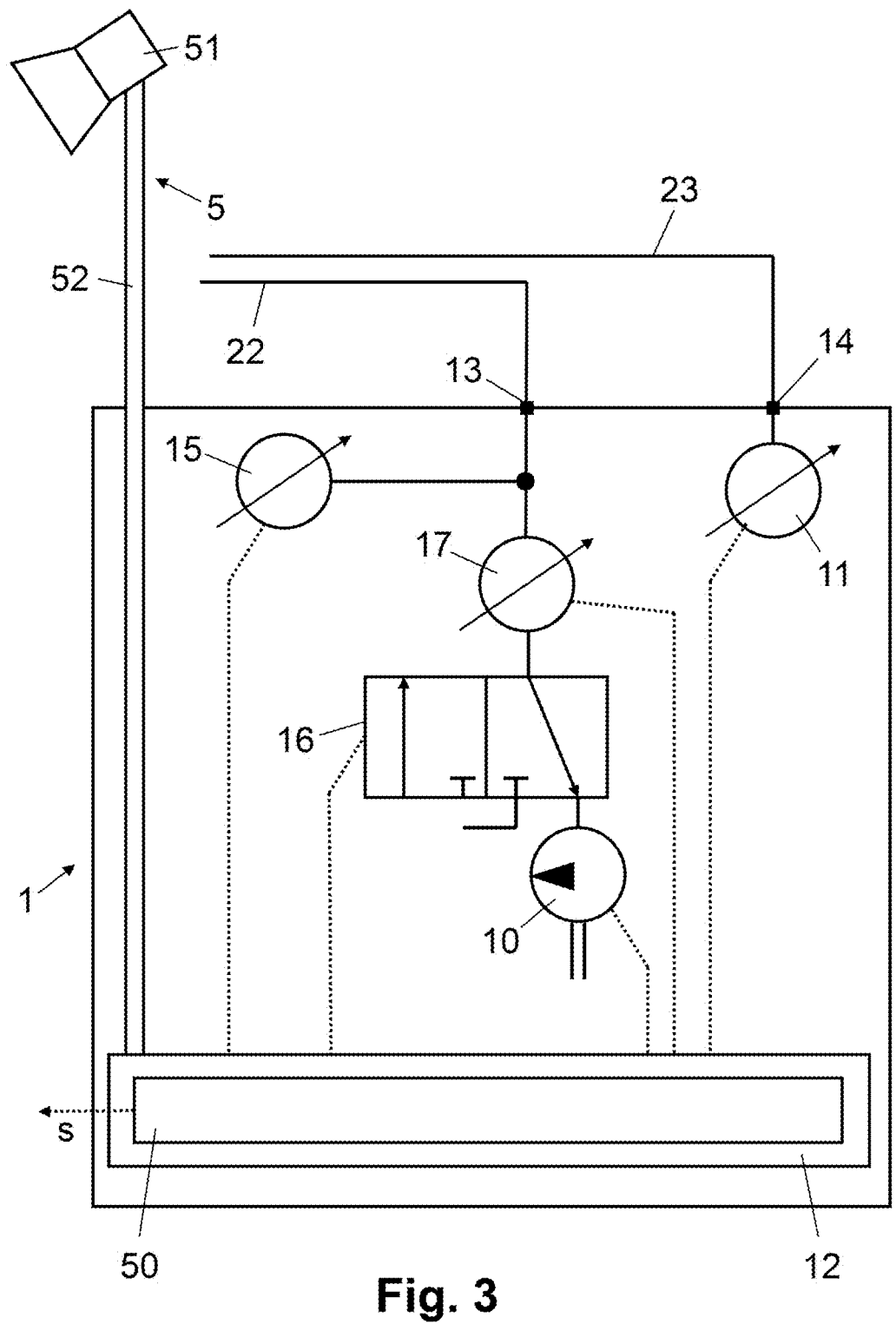
FIG. 3: shows a block diagram of a vacuum device comprising a vacuum generator and a vacuum interface for fluidically coupling the vacuum generator to a vacuum cavity of the patient interface.

FIG. 3 shows an exemplary embodiment of the vacuum device 1 which, in principle, has similar design to the vacuum device 1 in accordance with FIG. 1 but which, additionally, comprises a valve unit 16 that is operatively coupled to the control unit and actuated by the control unit 12.

By way of the valve unit 16, the vacuum supply line 22 is alternatively connected to the vacuum generator 10 (the position depicted here) for establishing and maintaining the vacuum or to the surroundings for ventilating and removing the vacuum in the vacuum cavity 20.

The embodiment of the vacuum device 11 depicted in FIG. 3 further comprises an optional flow sensor 17, which is fluidically arranged between the vacuum interface 13 and the valve unit 16. The flow sensor 17 serves to detect error states, in particular temporary or permanent leaks which cause an increased airflow when suctioning air out of the vacuum cavity 20. In the case of a pseudo-vacuum, in which a sufficient vacuum only appears to be present in the vacuum cavity 20 without in fact being present, for example on account of kinking of the vacuum connecting line 22 during the suction process at a point marked in an exemplary manner with "X" in FIG. 1 or caused by binding tissue or sterile covers, the second pressure sensor 15 measures a (normal) vacuum when the vacuum generator 10 is in operation; however, in comparison with the situation without pseudo-vacuum, there is no airflow, or only a reduced airflow, through the flow sensor 17 in this case, facilitating a detection of the pseudo-vacuum.

The embodiments of a vacuum device 1 depicted in FIG. 1 and FIG. 3 can be modified in various ways. Thus, instead of being arranged within a casing (not provided with a reference number) of the control unit 12, the pressure sensor 11 can be directly on, or in, the patient interface 2, with the pressure sensor connecting line 23 being dispensed with and, instead, an electric pressure sensor connecting line being provided. In such embodiments, the pressure sensor 11 can be e.g. a miniaturized disposable pressure sensor which e.g. is securely installed with the patient interface body 2' or the patient interface body 2' or the vacuum cavity 20 and the pressure sensor 11 have a fluidic interface, said interface being non-destructively detachable at least for the pressure sensor 11.

Instead of being on a casing of the vacuum device 1, the vacuum interface 13 and the pressure sensor interface 14 may also be situated on the interface to the patient interface body 2'. In this case, the vacuum connecting line 22 and the pressure sensor connecting line 23 can be wholly or partly part of the vacuum device 1. The fluidic interfaces 13, 14 can be realized by means of separate fluidic coupling units, for example separate fluidic plug-in connectors, or they can be integrated in a common fluidic coupling unit or plug-in connector.

The structure, in particular the fluidic structure, of the vacuum device 1 can be modified further and, in particular, comprise further components. Thus, the valve arrangement 16 as per FIG. 3 may comprise further valves and facilitate further fluidic configurations. Thus, provision can be made, for example, for the vacuum generator 10 to be fluidically connected to the surroundings. Further, provision can be made, for example, for the vacuum connecting line 22 to be fluidically terminated or fluidically isolated together with the connected second pressure sensor 15. Further, provision can be made of a vacuum reservoir with a volume in the region of e.g. one litre, said vacuum reservoir being connectable to the vacuum supply line 22 and/or the vacuum generator 10 by means of the valve arrangement. Such a vacuum reservoir serves, in particular, for fluidic buffering and can furthermore be used to suction away small amounts of air in place of, and with substantially the same function as, the vacuum generator, for example in the case of a relatively small and brief leak of the vacuum cavity 20. A vacuum in the optional vacuum reservoir is advantageously established by means of the vacuum generator 10.

Figure 4:
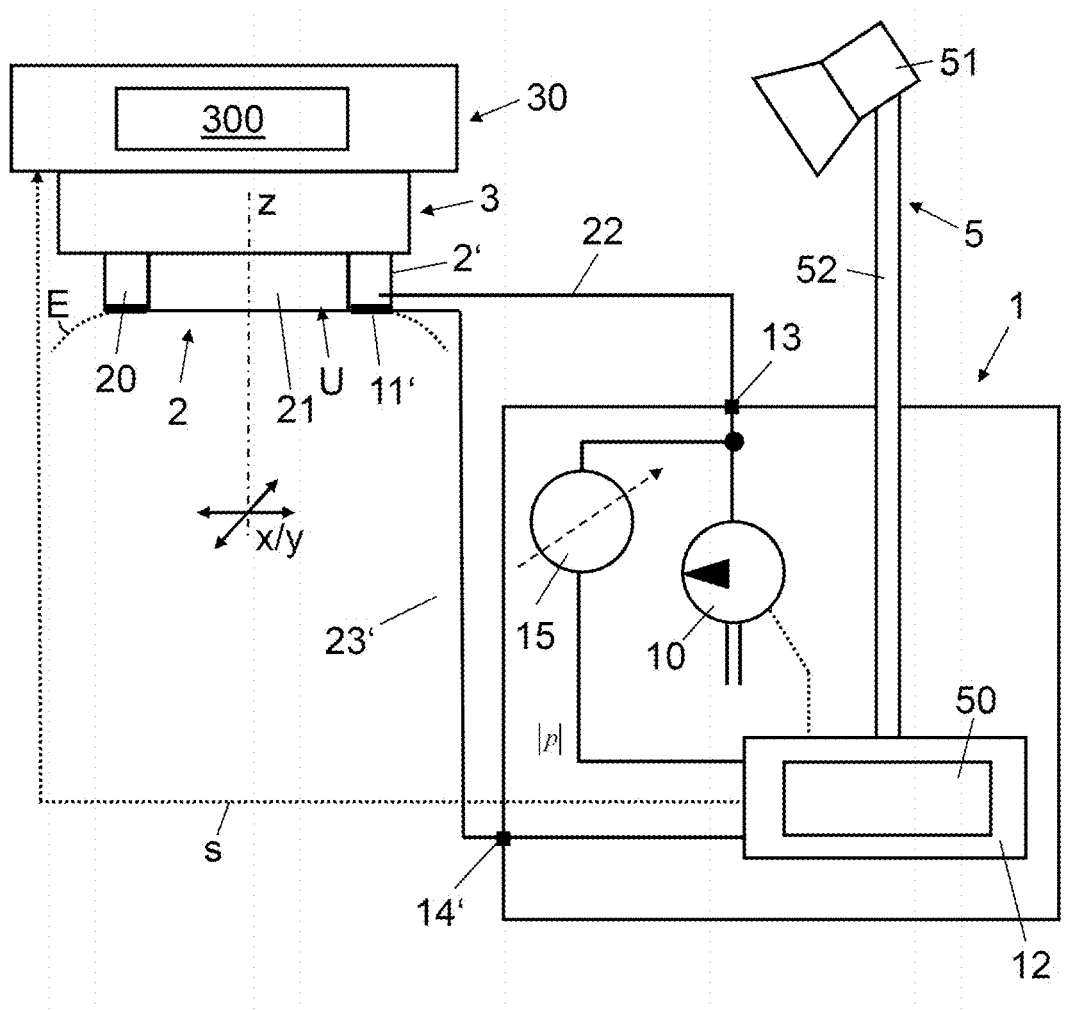
FIG. 4: shows a block diagram of a further ophthalmological arrangement comprising a vacuum device and a patient interface that is fluidically coupled therewith.

FIG. 4 illustrates a further embodiment of an ophthalmological arrangement comprising a further embodiment of the vacuum device 1 and a further embodiment of the patient interface 2 in a schematic functional illustration and in an operatively coupled state. Provided nothing else is stated to the contrary below, the vacuum device 1 and the patient interface 2 according to FIG. 4 may have an analogous structure to the illustration in accordance with FIG. 1 and a corresponding functionality.

In the embodiment in accordance with FIG. 4, the fluidic pressure sensor 11 is replaced by a contact pressure sensor 11' that is arranged in the patient interface 2. The contact pressure sensor 11' is designed to measure the contact pressure between the patient interface 2 and the patient's eye E and is, in an exemplary fashion, integrated in a ring-shaped manner in the side of a wall of the suction ring that faces the patient's eye E. Alternatively, provision can also be made of a plurality of isolated contact pressure sensors along the circumference of the suction ring, or else only of an individual isolated contact pressure sensor.

In this form, the fluidic pressure sensor connecting line 23 of FIG. 1 is replaced by an electric pressure sensor connecting ling 23', by means of which the contact pressure sensor 11' is coupled to the vacuum device 1 in a functionally electric manner. Accordingly, an electrical device-side pressure sensor interface 14', e.g. in the form of an electrical plug-in connector, is provided instead of the fluidic device-side pressure sensor interface 14 in accordance with FIG. 1. Optionally, a fluidic pressure sensor 11 in accordance with FIG. 1 may additionally be provided.

As illustrated schematically in FIGS. 1, 3 and 4, the control unit 12 or the processing unit 50 is connected to the vacuum generator 10 via an (electrical) control line and to the pressure sensors 11, 15 or the contact pressure sensors 11' via (electrical) signal lines.

For the purposes of coupling the patient interface 2 to the patient's eye E, the vacuum generator 10 is actuated or put into operation by the control unit 12 such that the air that is originally present in the vacuum cavity 20 is at least partly suctioned away. The pressure sensor 11 that is coupled to the vacuum cavity 20 in a functionally separate manner measures the pressure that is effectively present in the vacuum cavity 20 in a manner that is independent of the vacuum connecting line 22 (alternatively, one or more contact sensors 11' measure the contact pressure).

Figure 5:
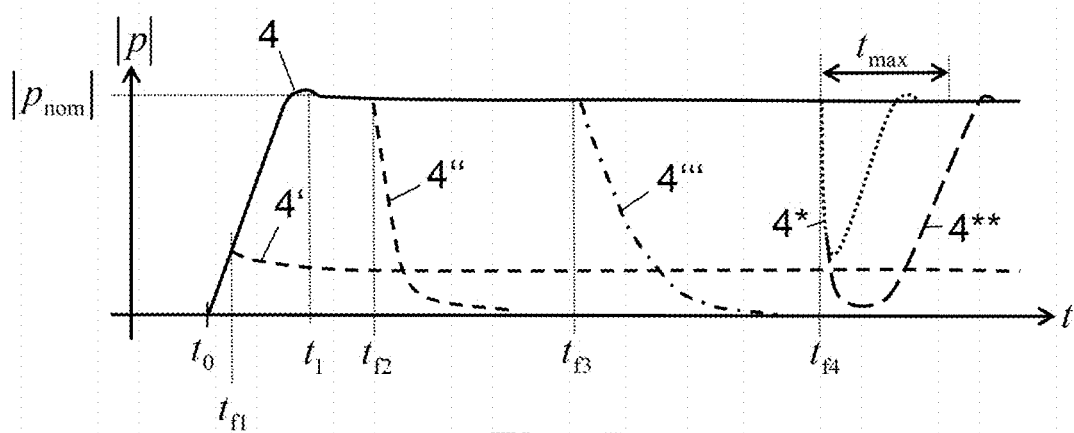
FIG. 5: shows various pressure curves as a function of time.

In FIG. 5, the curve denoted by the reference sign 4 plots the absolute value of the vacuum p, as measured by the pressure sensor 11, as a function of time t for a correct affixment of the patient interface 2 on the patient's eye E. Here, a value of p=0 corresponds to the ambient pressure and an increasing vacuum (decreasing absolute pressure) corresponds to an increasing curve profile.

In the suctioning phase, which starts at the time $t_0$, air that is present in the vacuum cavity 20 is suctioned out through the vacuum connecting line 22 by way of the vacuum generator 10, as a result of which the vacuum increases. In the case of an intended vacuum that corresponds to the envisaged operating state, for example of $p_{nom}$=−400 mbar, the control unit 12 switches to a stationary holding operation at the time $t_1$ in a manner known per se, during which the vacuum in the vacuum cavity 20 is kept substantially constant. This state is maintained until pressure equalization with the surroundings is established as desired and the patient interface 2 is thus released from the cornea of the patient's eye E.

The air flow out of the vacuum cavity 20 in the direction of the vacuum device 1 or of the vacuum generator 10, which arises when suctioning the air out of the vacuum cavity 20, moreover brings about a removal of possibly present liquid droplets, residue of sterile cover films, etc., from the region of the coupling between the pressure sensor connecting line 23 and the vacuum cavity 20.

The curve 4' in FIG. 5 schematically shows the pressure p that is measured by the pressure sensor 11 if, at a first error time, time $t_{f1}$, a pseudo-vacuum in accordance with the type described above arises. A pressure sensor 15 that is connected in the vacuum device 1 to the vacuum connecting line 22, as is typically present according to the prior art and as is optional in the vacuum device 1 shown in FIG. 1, cannot detect the kinking of the vacuum connecting line 22 since a vacuum is still present between the location of the kinking and the vacuum device 1, or the vacuum generator 10, or said vacuum continues to be built up, and hence a vacuum is measured by the pressure sensor 15, said vacuum however not being present in the vacuum cavity 20. On account of the direct coupling of the pressure sensor 11 to the vacuum cavity 20, which is independent of the vacuum connecting line 22, the pressure sensor 11 by contrast measures the pressure that is effectively present in the vacuum cavity 20. Accordingly, the vacuum as measured by the pressure sensor 11 does not continue to rise after the vacuum connecting line 22 has kinked, even though the vacuum generator 10 continues to operate. The vacuum in the vacuum cavity 20 remains substantially constant (at a level that is too low) after the occurrence of the pseudo-vacuum or it reduces again on account of elasticity and/or possibly present leaks such that pressure equalization with the surroundings occurs.

The curve 4" in FIG. 5 represents the pressure that is measured by the pressure sensor 11 in the case where the vacuum in the vacuum cavity 20 is lost (after the vacuum has initially been established correctly and after a correct affixment of the patient interface 2 on the patient's eye E) at a second error time $t_{f2}$ during stationary operation. By way of example, this is the case if the patient interface 2 briefly and partly detaches from the patient's eye E, as may occur in inexpedient cases, e.g. on account of a required movement of the patient interface by the ophthalmologist or a movement of the patient themselves. In this case, there is at least partial pressure equalization with the surroundings and hence a loss of the vacuum in the vacuum cavity 20. In principle, this pressure drop-off can be detected by the pressure sensor 15 and the vacuum generator 10 can re-establish the correct vacuum, at least in the case of only a brief leak. However, if the vacuum connecting line 22 itself is kinked or not continuous for any other reason, then the loss of the vacuum is not identified by the pressure sensor 15. In the case of an only partly continuous vacuum connecting line 22, there is at least an increase in the control delay when correcting the pressure drop such that a secure affixment of the patient interface 2 on the patient's eye E likewise can no longer be provided, or at least cannot be ensured, in certain circumstances. However, the pressure sensor 11 that is directly connected to the vacuum cavity 20 correctly identifies the loss of the vacuum in accordance with curve 4".

The curve 4''' in FIG. 5 represents the case where the vacuum (after the vacuum has initially been established correctly and after a correct affixment of the patient interface 2 on the patient's eye E) is lost slowly (in comparison with the profile depicted in curve 4") at a third error time $t_{f3}$, which may be caused, for example, by a small leak in, or a defective tightness of, a fluidic connector.

The curves 4* and 4** in FIG. 5 represent cases where the vacuum (after the vacuum has initially been established correctly and after a correct affixment of the patient interface 2 on the patient's eye E) is lost briefly and temporarily at a fourth error time $t_{f4}$, which may be caused, for example, by a temporary blocking of the vacuum connecting line 22—but also of the pressure sensor connecting line 23. As can be seen in the case of curve 4*, the intended vacuum $p_{nom}$, corresponding to the intended operating state, is re-established within a time duration which lies before (or within) a predetermined maximum time duration $t_{max}$. By contrast, in the case of the curve 4**, the intended vacuum $p_{nom}$ is only reached again after the maximum time duration $t_{max}$ has elapsed.

Figure 6:
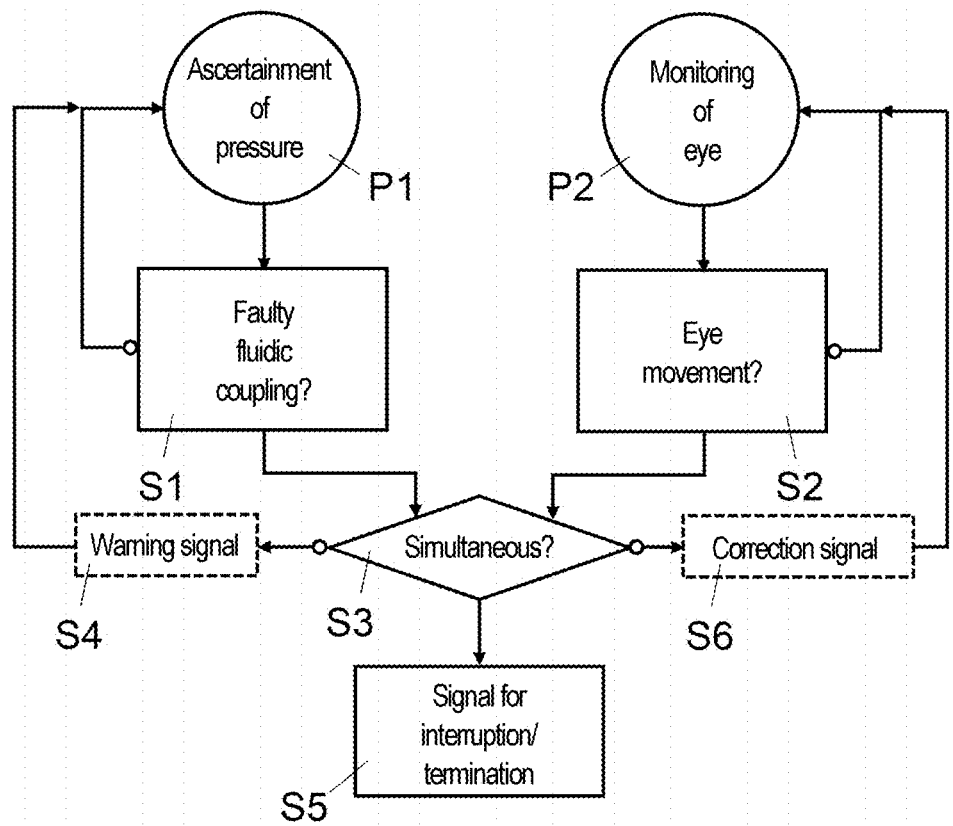
FIG. 6: shows a flowchart which illustrates processes and steps for monitoring an ophthalmological patient interface.

FIG. 6 schematically illustrates processes P1, P2 and steps S1, S2, S3, S4, S5 for monitoring the ophthalmological patient interface 2.

In process P1, there is continuous or virtually continuous ascertainment of the pressure (vacuum) in the vacuum cavity 20. Depending on the embodiment variant and configuration, the pressure in process P1 is ascertained by the pressure sensor 11, alternatively by one or more contact pressure sensors 11', optionally additionally by one or more (redundant) contact pressure sensors 11', and optionally additionally by the (redundant) pressure sensor 15.

In step S1, the processing unit 50 determines whether there is a faulty fluidic coupling of the patient interface 2 or of the vacuum cavity 20 on the basis of the pressure values ascertained in process P1. Here, the measured pressure is compared continuously or virtually continuously to at least one limit vacuum $p_{limit}$. This limit pressure $p_{limit}$ typically lies lower than the intended vacuum $p_{nom}$ in terms of magnitude and can e.g. be effectuated by the magnitude of the intended vacuum $p_{nom}$ minus a safety value that is determined by tolerances, measurement uncertainty, etc. In the suctioning phase, the limit pressure $p_{limit}$ may be continuously adapted in accordance with the pressure curve that results in the case of correct operation. Then, an error case is assumed if the limit pressure $p_{limit}$ is undershot.

Alternatively, or in a complementary manner, the measured pressure is evaluated continuously or virtually continuously in respect of a loss, or fall, of the vacuum. To this end, numerous methods from signal processing and/or statistics, which are known per se, may be used, for example determining and evaluating the gradient and/or further characteristics of a function formed by an interpolation of measurement values.

If the vacuum device 1 additionally comprises the optional second pressure sensor 15, the detection of faulty fluidic coupling of the patient interface 2 is alternatively carried out, or carried out in a complementary manner, by a comparison or a common evaluation of the pressures ascertained by the pressure sensor 11 and the second pressure sensor 15. In the case of correct coupling of the patient interface 2 and without the presence of an error state, the pressures measured by the pressure sensor 11 and the second pressure sensor 15 are substantially the same, at least during the stationary operating state, and the sensors 11, 15 are consequently redundant. Accordingly, the detection of faulty or insufficient fluidic coupling of the patient interface 2 may comprise the detection of a deviation between the pressures ascertained by the pressure sensor 11 and the second pressure sensor 15. Here, the deviation may be ascertained by means of methods from signal processing and/or statistics, which are known per se, and may comprise e.g. an ascertainment and evaluation of a difference of the ascertained pressures and the comparison with an admissible maximum difference, which is typically determined from tolerances and measurement uncertainties. As an alternative, or in a complementary manner, to forming the difference, determining faulty or insufficient coupling may e.g. comprise the ascertainment and evaluation of a correlation of the pressures ascertained by the pressure sensor 11 and the second pressure sensor 15 as a function of the time t.

In one embodiment variant, the control device 12 or the processing unit 50 takes into account the time duration during which a pressure drop is determined when detecting faulty fluidic coupling of the patient interface 2 in order to not unnecessarily interrupt an ophthalmological laser treatment on account of a brief, temporary pressure drop which does not cause an interfering detachment or displacement of the patient interface 2 from or relative to the patient's eye E. Here, a brief, temporary pressure drop which again lies above the required limit pressure $p_{limit}$ within a predetermined maximum time duration $t_{max}$ is not treated as faulty fluidic coupling of the patient interface 2, at least not if such brief, temporary pressure drops do not repeat with a limit-overshooting frequency (oscillation behaviour).

In the case of a common evaluation of the pressures ascertained by the pressure sensor 11 and the second pressure sensor 15, it should be noted that the pressure sensor 11 reacts more quickly to pressure changes in the vacuum cavity 20 than the second vacuum sensor 15, in particular when establishing the vacuum in the vacuum cavity 20 and when ventilating. This emerges from the fact that there simultaneously is a displacement of an air volume by way of the vacuum connecting line 22 while the pressure sensor connecting line 23 is fluidically closed by the pressure sensor 11.

An advantage emerging from the common evaluation of the pressures ascertained by the pressure sensor 11 and the second pressure sensor 15 is that the control device 12 or the processing unit 50 is moreover able to detect further error states, for example a pseudo-vacuum of the pressure sensor connecting line 23 or defects of the pressure sensors 11, 15, the electrical contacting thereof and/or components disposed downstream thereof.

In process P2 there is continuous or virtually continuous (video) monitoring of the patient's eye E by the sensor device(s) 51 of the movement detector 5.

In step S2, the processing unit 50 detects movements of the patient's eye E on the basis of the monitoring that took place in process P2 (video monitoring, video capture, OCT measurement, triangulation, etc.) or on the basis of the measurement signals (e.g. video signals) that were supplied in process P2 by the sensor device(s) 51.

In step S3, the processing unit 50 examines whether there is a detected movement of the patient's eye E at the same time as a detected faulty fluidic coupling of the patient interface 2. If this is not the case, the continuous ascertainment of the pressure in the vacuum cavity 20 in process P1 and the continuous monitoring of the patient's eye E in process P2 is continued, without the ophthalmological treatment being interrupted or terminated by the ophthalmological treatment device 30.

In the optional step S4, the processing unit 50 produces a warning signal which indicates that a faulty fluidic coupling of the patient interface 2 was detected. For this purpose, the control unit 12 comprises an alarm device or is connected to an alarm device (not depicted) which is configured to produce an optical and/or acoustic alarm on the basis of the warning signal.

In the optional step S6, the processing unit 50 produces a correction signal for the ophthalmological treatment device 30 or the laser system 300 after the eye was detected if no faulty fluidic coupling of the vacuum cavity 20 is detected. The correction signal allows the ophthalmological treatment device 30 or the laser system 300 to realign or position the laser beam or the focus thereof, taking into account the detected eye movement and the intended position (as per the control data of the ophthalmological treatment) and to continue the ophthalmological treatment if no faulty fluidic coupling of the vacuum cavity 20 is detected. The correction signal comprises a specification of the detected eye movement, for example the current (actual) orientation of the patient's eye E or a displacement vector which defines the movement of the patient's eye E, proceeding from its initial orientation prior to the detected eye movement to its actual position after the detected eye movement, and which facilitates a correction for the ophthalmological treatment device 30 or the laser system 300 with a realignment of the laser beam or repositioning of the focus thereof.

If a faulty fluidic coupling of the patient interface 2 and an eye movement of the patient are determined at the same time, the processing unit 50 produces a control signal s in step S5 for interrupting the ophthalmological treatment carried out by the ophthalmological treatment device 30. As depicted schematically in FIGS. 1 and 4, the control signal s is fed by the control unit 12 or the processing unit 50 via a signal line of the ophthalmological treatment device 30. To this end, the control unit 12 or the processing unit 50 is connected to the ophthalmological treatment device 30 or arranged in the ophthalmological treatment device 30, for example in the application head 3. In the ophthalmological treatment device 30, the ophthalmological treatment is interrupted or terminated on account of the incoming control signal by virtue of, for example, the laser system 300 being switched off and/or the laser beam being interrupted by moving a stop or a shutter. Moreover, the control unit 12 or the processing unit 50 produces an alarm signal, as was described above in conjunction with the warning signal of step S4.

The invention claimed is:

1. A vacuum device for affixing an ophthalmological patient interface on a patient's eye, the vacuum device comprising:
    a vacuum generator and a vacuum interface, the vacuum interface being configured to fluidically couple the vacuum generator to a vacuum cavity of the ophthalmological patient interface;
    at least one of: an internal pressure sensor and a pressure-measuring interface, the internal pressure sensor being configured to be fluidically coupled to the ophthalmological patient interface, and the pressure-measuring interface being configured to receive a signal from an external pressure sensor of the ophthalmological patient interface;
    a movement detector which is configured to detect movements of the patient's eye, whereby the movement detector comprises a light transmitter and light detectors for optical coherence tomography and is configured to use the optical coherence tomography to execute repeatedly spatial scans on the patient's eye for detecting the movements of the patient's eye; and
    a control unit which is connected to an ophthalmological treatment device via a signal line and comprises an electronic circuit configured to detect a faulty fluidic coupling of the vacuum generator to the vacuum cavity by determining whether a pressure that is ascertained by either the internal pressure sensor or the external pressure sensor, during an ophthalmological treatment that is carried out by the ophthalmological treatment device, is below a reference pressure for a duration longer than a predetermined maximum time duration, indicative of a prolonged loss of pressure, to examine continuously the spatial scans of the patient's eye with respect to deviations indicative of movements of the patient's eye, and to produce and transmit to the ophthalmological treatment device via the signal line a control signal for interrupting the ophthalmological treatment that is carried out by the ophthalmological treatment device when an eye movement is detected at the same time as the faulty fluidic coupling of the vacuum generator to the vacuum cavity is detected with a prolonged loss of pressure.

2. The vacuum device according to claim 1, wherein the control unit is configured to produce a warning signal without interrupting the ophthalmological treatment when no eye movement is detected during a detected faulty fluidic coupling of the vacuum generator to the vacuum cavity.

3. The vacuum device according to claim 1, wherein the movement detector further comprises a video sensor and a processing unit that is connected to the video sensor and configured to detect the eye movements on a basis of video signals supplied by the video sensor.

4. The vacuum device according to claim 1, wherein the movement detector is configured to detect eye movements relative to a static observation axis, in a first movement direction in a plane to which the observation axis is normal and in a second movement direction along the observation axis.

5. The vacuum device according to claim 1, wherein the control unit is configured to produce the control signal for interrupting the ophthalmological treatment when the movement detector detects an eye movement that lies over a defined tolerance threshold.

6. The vacuum device according to claim 1, wherein the vacuum device comprises a pressure sensor interface that has a fluidic connection to the internal pressure sensor, the pressure sensor interface being configured to fluidically couple the internal pressure sensor to the ophthalmological patient interface, separately from the vacuum interface.

7. The vacuum device according to claim 1, wherein the pressure-measuring interface is configured to receive a signal from an external contact pressure sensor that is arranged at the ophthalmological patient interface.

8. The vacuum device according to claim 1, wherein the control unit is configured to detect the faulty fluidic coupling of the vacuum generator to the vacuum cavity by detecting a drop in the pressure, that is ascertained by either the internal pressure sensor or the external pressure sensor, as a function of time.

9. The vacuum device according to claim 1, wherein the vacuum device comprises a second pressure sensor that is fluidically coupled to the vacuum interface and connected to the control unit, and the control unit is configured to detect the faulty fluidic coupling of the vacuum generator to the vacuum cavity by comparing the pressure, that is ascertained by either the internal pressure sensor or the external pressure sensor, with a second pressure, that is ascertained by the second pressure sensor.

10. The vacuum device according to claim 1, wherein the movement detector further comprises a sensor device that is configured to detect the eye movements on a basis of changes in a distance of the patient's eye relative to the ophthalmological patient interface.

11. The vacuum device according to claim 1, wherein the control unit is configured to produce a correction signal for repositioning and continuing the ophthalmological treatment on a basis of a detected eye movement when a termination of the eye movement and no faulty fluidic coupling of the vacuum cavity are detected.

12. A method of monitoring an ophthalmological patient interface which is affixed on a patient's eye by means of a vacuum that is produced by a vacuum generator in a vacuum cavity of the ophthalmological patient interface, the method comprising:
    ascertaining a pressure by using a first pressure sensor that is fluidically coupled to the ophthalmological patient interface and/or by using a second pressure sensor arranged at the ophthalmological patient interface, during an ophthalmological treatment that is carried out by an ophthalmological treatment device;

detecting movements of the patient's eye by means of a movement detector which comprises a light transmitter and light detectors for optical coherence tomography and uses the optical coherence tomography to execute repeatedly spatial scans of the patient's eye for detecting the movements of the patient's eye;

detecting a faulty fluidic coupling of the vacuum generator to the vacuum cavity by an electronic circuit of a control unit determining whether a pressure that is ascertained by either the first pressure sensor or the second pressure sensor, is below a reference pressure for a duration longer than a predetermined maximum time duration, indicative of a prolonged loss of pressure;

examining continuously by the control unit the spatial scans of the patient's eye with respect to deviations indicative of movements of the patient's eye; and producing and transmitting the ophthalmological treatment device via a signal line by the electronic circuit of the control unit a control signal for interrupting the ophthalmological treatment that is carried out by the ophthalmological treatment device when an eye movement is detected at the same time as the faulty fluidic coupling of the vacuum generator to the vacuum cavity is detected with a prolonged loss of pressure.

13. The method according to claim 12, further comprising producing, by the control unit, a warning signal without interrupting the ophthalmological treatment when no eye movement is detected during a detected faulty fluidic coupling of the vacuum generator to the vacuum cavity.

14. The method according to claim 12, wherein the method further comprises capturing a video of the patient's eye by a video sensor and detecting of the eye movements by the control unit on a basis of the video capture.

15. The method according to claim 12, further comprising producing, by the control unit, the control signal for interrupting the ophthalmological treatment when the movement detector detects an eye movement that lies over a defined tolerance threshold.

16. An ophthalmological treatment device comprising a laser system for the ophthalmological treatment of a patient's eye, an application head and an ophthalmological patient interface for attaching the application head to the patient's eye, wherein the ophthalmological treatment device further comprises:

a vacuum device for affixing the ophthalmological patient interface on the patient's eye, the vacuum device comprising a vacuum generator and a vacuum interface, the vacuum interface being configured to fluidically couple the vacuum generator to a vacuum cavity of the ophthalmological patient interface;

a pressure sensor arranged at the ophthalmological patient interface;

a movement detector which is configured to detect movements to the patient's eye, whereby the movement detector comprises a light transmitter and light detectors for optical coherence tomography and is configured to use the optical coherence tomography to execute repeatedly spatial scans of the patient's eye for detecting the movements of the patient's eye; and a control unit comprising an electronic circuit configured to detect a faulty fluidic coupling of the vacuum generator to the vacuum cavity by determining whether a pressure that is ascertained by the pressure sensor, during an ophthalmological treatment that is carried out by the ophthalmological treatment device, is below a reference pressure for a duration longer than a predetermined maximum time duration, indicative of a prolonged loss of pressure, to examine continuously the spatial scans of the patient's eye with respect to deviations indicative of movements of the patient's eye, and to produce for the ophthalmological treatment device a control signal for interrupting the ophthalmological treatment that is carried out by the ophthalmological treatment device when an eye movement is detected at the same time as the faulty fluidic coupling of the vacuum generator to the vacuum cavity is detected with a prolonged loss of pressure.

17. The ophthalmological treatment device of claim 16, wherein the control unit further is configured to produce a warning signal without interrupting the ophthalmological treatment when no eye movement is detected during a detected faulty fluidic coupling of the vacuum generator to the vacuum cavity.

18. The ophthalmological treatment device of claim 16, wherein the movement detector further comprises a video sensor and a processing unit that is connected to the video sensor and configured to detect the eye movements on a basis of video signals supplied by the video sensor.

19. The ophthalmological treatment device of claim 16, wherein the movement detector further comprises a sensor device that is configured to detect the eye movements on a basis of changes in a distance of the patient's eye relative to the ophthalmological patient interface.

20. The ophthalmological treatment device of claim 16, wherein the control unit is configured to produce a correction signal for repositioning and continuing the ophthalmological treatment on a basis of a detected eye movement when a termination of the eye movement and no faulty fluidic coupling of the vacuum cavity are detected.

21. A vacuum device for affixing an ophthalmological patient interface on a patient's eye, the vacuum device comprising:

a vacuum generator and a vacuum interface, the vacuum interface being configured to fluidically couple the vacuum generator to a vacuum cavity of the ophthalmological patient interface;

at least one of: an internal pressure sensor and a pressure-measuring interface, the internal pressure sensor being configured to be fluidically coupled to the ophthalmological patient interface, and the pressure-measuring interface being configured to receive a signal from an external pressure sensor of the ophthalmological patient interface;

a movement detector which is configured to detect movements of the patient's eye; and a control unit which is connected to an ophthalmological treatment device via a signal line and comprises an electronic circuit configured to detect a faulty fluidic coupling of the vacuum generator to the vacuum cavity by determining whether a pressure that is ascertained by either the internal pressure sensor or the external pressure sensor, during an ophthalmological treatment that is carried out by the ophthalmological treatment device, is below a reference pressure for a duration longer than a predetermined maximum time duration, indicative of a prolonged loss of pressure, and to produce and transmit to the ophthalmological treatment device via the signal line a control signal for interrupting the ophthalmological treatment that is carried out by the ophthalmological treatment device when an eye movement is detected by the movement detector at the same time as the faulty fluidic coupling of the vacuum generator to the vacuum cavity is detected with a prolonged loss of pressure.

22. A method of monitoring an ophthalmological patient interface which is affixed on a patient's eye by means of a vacuum that is produced by a vacuum generator in a vacuum cavity of the ophthalmological patient interface, the method comprising:

ascertaining a pressure by using a first pressure sensor that is fluidically coupled to the ophthalmological patient interface and/or by using a second pressure sensor arranged at the ophthalmological patient interface, during an ophthalmological treatment that is carried out by an ophthalmological treatment device;

detecting movements of the patient's eye by means of a movement detector;

detecting a faulty fluidic coupling of the vacuum generator to the vacuum cavity by an electronic circuit of a control unit determining whether a pressure that is ascertained by either the first pressure sensor or the second pressure sensor, is below a reference pressure for a duration longer than a predetermined maximum time duration, indicative of a prolonged loss of pressure; and producing and transmitting to the ophthalmological treatment device via a signal line by the electronic circuit of the control unit a control signal for interrupting the ophthalmological treatment that is carried out by the ophthalmological treatment device when an eye movement is detected by the movement detector at the same time as the faulty fluidic coupling of the vacuum generator to the vacuum cavity is detected with a prolonged loss of pressure.

23. An ophthalmological treatment device comprising a laser system for the ophthalmological treatment of a patient's eye, an application head and an ophthalmological patient interface for attaching the application head to the patient's eye, wherein the ophthalmological treatment device further comprises:

a vacuum device for affixing the ophthalmological patient interface on the patient's eye, the vacuum device comprising a vacuum generator and a vacuum interface, the vacuum interface being configured to fluidically couple the vacuum generator to a vacuum cavity of the ophthalmological patient interface;

a pressure sensor arranged at the ophthalmological patient interface;

a movement detector which is configured to detect movements to the patient's eye; and a control unit comprising an electronic circuit configured to detect a faulty fluidic coupling of the vacuum generator to the vacuum cavity by determining whether a pressure that is ascertained by the pressure sensor, during an ophthalmological treatment that is carried out by the ophthalmological treatment device, is below a reference pressure for a duration longer than a predetermined maximum time duration, indicative of a prolonged loss of pressure, and to produce for the ophthalmological treatment device a control signal for interrupting the ophthalmological treatment that is carried out by the ophthalmological treatment device when an eye movement is detected by the movement detector at the same time as the faulty fluidic coupling of the vacuum generator to the vacuum cavity is detected with a prolonged loss of pressure.

\* \* \* \* \*